United States Patent [19]
Maki et al.

[11] Patent Number: 5,586,554
[45] Date of Patent: Dec. 24, 1996

[54] OPTICAL SYSTEM FOR MEASURING METABOLISM IN A BODY

[75] Inventors: Atsushi Maki, Hachioji; Fumio Kawaguchi, Tokyo; Yuichi Yamashita, Hachioji; Yoshitoshi Ito, Ome, all of Japan

[73] Assignee: Hitachi, Ltd., Tokyo, Japan

[21] Appl. No.: 197,749

[22] Filed: Feb. 16, 1994

[30] Foreign Application Priority Data

Feb. 23, 1993 [JP] Japan .................................. 5-033018

[51] Int. Cl.$^6$ ............................................. A61B 5/05
[52] U.S. Cl. ...................... 128/653.1; 128/664; 128/665; 128/633
[58] Field of Search ................................. 128/664, 665, 128/633; 356/338, 343; 250/574

[56] References Cited

U.S. PATENT DOCUMENTS

| | | | |
|---|---|---|---|
| 4,281,645 | 8/1981 | Jöbsis | 128/633 |
| 4,651,743 | 3/1987 | Stoller | 128/665 |
| 5,088,493 | 2/1992 | Giannini et al. | 128/664 |
| 5,090,415 | 2/1992 | Yamashita et al. | 128/665 |
| 5,148,022 | 9/1992 | Kawaguchi et al. | 250/341 |
| 5,303,026 | 4/1994 | Strobl et al. | 356/318 |
| 5,318,022 | 6/1994 | Taboada et al. | 128/665 |
| 5,349,951 | 9/1994 | Ito et al. | 128/665 |
| 5,361,758 | 11/1994 | Hall et al. | 128/665 |
| 5,379,764 | 1/1995 | Barnes et al. | 128/664 |
| 5,416,582 | 5/1995 | Knutson et al. | 128/665 |
| 5,447,159 | 9/1995 | Schultz | 128/664 |

FOREIGN PATENT DOCUMENTS

| | | | |
|---|---|---|---|
| 0352923 | 1/1990 | European Pat. Off. | 128/633 |
| 0358809 | 3/1990 | European Pat. Off. | 128/633 |
| 55-24004 | 6/1978 | Japan . | |
| 0199430 | 3/1984 | Japan . | |
| 3016629 | 9/1993 | WIPO | 128/633 |

*Primary Examiner*—Marvin M. Lateef
*Assistant Examiner*—Brian L. Casler
*Attorney, Agent, or Firm*—Antonelli, Terry, Stout & Kraus

[57] ABSTRACT

An optical system is arranged to irradiate light to the inside of a test subject and detect the light passed through the test subject for obtaining information about the inside of the test subject. The optical system includes a light source for generating rays of light having different wavelengths, an apparatus for irradiating the rays of light to corresponding spots on the test subject, an apparatus for detecting the light passed through the test subject at plural detecting spots on the test subject, and an apparatus for dispersing the detected light. The rays of light to be irradiated to the test subject have a visible wavelength to a near infrared one. The apparatus for irradiating light operates to irradiate the rays of light of each of the wavelengths to the test subject substantially at one time or by shifting the irradiating times according to each of the wavelengths. The apparatus for irradiating light contains the apparatus for dispersing the irradiated light into respective wavelengths. The rays of light dispersed by the dispersing apparatus are irradiated to the test subject.

34 Claims, 10 Drawing Sheets

OPTICAL SYSTEM FOR MEASURING METABOLISM IN A BODY

BACKGROUND OF THE INVENTION

The present invention relates to an optical system for measuring metabolism in a body or test subject which is arranged to have each of a large number of points arranged for irradiating a ray of light located outside of the test subject so as to identify the material inside of the test subject and measure the amount of the material or display it as an image.

There has been heretofore proposed an oximeter as an optical system for measuring metabolism in a body or an optical CT as an optical apparatus for measuring an image. The conventional optical CT is arranged to display a tomographic image standing for oxygen saturation in a living body by using absorption spectra of oxyhemoglobin. The measuring method employed by this optical CT includes the steps of irradiating rays of light onto the body one by one, detecting the light passed through the body, deriving light absorption of hemoglobin distributed inside of the body based on the intensity of the detected beam, and obtaining a tomographic image standing for oxygen saturation. U.S. Pat. Nos. 4,281,645 and 5,148,022 disclose optical CT systems which measure biodynamics such as metabolism or circulation and display the measured result as an image by using a visible ray less body-injurious than to an infrared one. As an optical apparatus for measuring biodynamics, the J-P-A-60-199430 discloses an optical apparatus for measuring speed of blood flow from a reflected beam by the effect of a laser speckle method. Moreover, oximeter for measuring an oxygen density in blood by using a beam passed through a part of the body has been disclosed in J-P-A-55-24004.

SUMMARY OF THE INVENTION

Consider a measuring apparatus arranged to use the light passed through a test subject as a detection signal. In this case, the signal intensity of the passed beam is made weaker in proportion to the size of the test subject. The measurement, therefore, needs a lot of time. In particular, to obtain data required for creating an image standing for distribution of a material amount, it is necessary to take the operating steps of sequentially irradiating rays of light to a large number of spots on the test subject and defecting of the light passed through the test subject at a large number of locations on the test subject. The operation needs a very long measuring time. If the material amount in the test subject varies with time, the measuring time is made too long to follow the variation of the material amount. Then, consider an optical system for measuring metabolism in diagnosing a human body. In this case, such a long measuring time causes the great pain to a human body.

It is an object of the present invention to provide an optical system for measuring metabolism in a body which is arranged to reduce the measuring time in order to solve various problems derived from the long measuring time.

In achieving object, an optical system for measuring metabolism in a body according to the present invention includes a light source for generating rays of light having respective wavelengths, an apparatus for irradiating light to a single or plural spots of a test subject from the light source at one time, an apparatus for detecting light passed through the test subject at detecting spots at one time, and an apparatus for separating the detected light by wavelengths. Further, the optical system for measuring metabolism in a body provides a light source for generating pulses of light having respective wavelengths, an apparatus for irradiating plural pulses of lights having respective wavelengths to a single or plural spots of a test subject at one time or at sequential times, an apparatus for detecting the light passed through the test subject at the detecting spots at one time, and an apparatus for separating the detected light by wavelength. Moreover, the optical system for measuring metabolism in a body provides a single or plural light sources for generating lights having respective wavelengths, a single or plural spectroscopes for separating the light having respective wavelengths substantially at one time, a single or plural light detectors for detecting the intensity of the light passed through the test subject or the aging of the intensity at each detecting spot substantially at one time, and means for transmitting light, composed of an optical fiber.

An optical system for measuring metabolism in a body according to the present invention arranged to irradiate light to the inside of the test subject and measure light absorption inside of the test subject and distribution of scattering characteristics includes a light source for generating rays of light having respective wavelengths, an apparatus for irradiating the rays of light having respective wavelengths to a single or plural spots of the test subject, an apparatus for detecting a light(s) passed through the test subject at a single or plural spots of the test subject, and an apparatus for separating the detected light by wavelength. This optical system for measuring metabolism in a body has the following features.

(1) The apparatus for irradiating light operates to irradiate lights having respective wavelengths to a single or plural spots of the test subject substantially at one time.

(2) The apparatus for irradiating light provides a single or plural light switches for switching the wavelengths of lights irradiated to the spots of the test subject and operates to irradiate pulses of lights having respective wavelengths to a single or plural spots of the test subject as the irradiating times are shifted according to each of the wavelengths.

(3) The light separates by the apparatus for separating light irradiated from the light source into plural equally spaced wavelengths is irradiated to the test subject.

(4) The intensity of the light obtained by separating the wavelength of the passed light or the aging of the intensity is detected.

(5) The spot of the test subject where light is irradiated is specified by the wavelength of the light. The material amount distributed inside of the test subject obtained by the operation or the value (amount) derived from the changing material amount is displayed as a two-dimensional tomographic image or a three-dimensional image.

(6) The distribution of the material amount inside of the test subject or the distribution of an absorption characteristic or a scattering characteristic or an index characteristic is derived as a two-dimensional tomographic image or a three-dimensional image.

(7) Rays ranging from a visible ray to a near infrared one are irradiated to the test subject. The lights passed through the test subject are measured so as to display as an image the distribution of a scattering characteristic or an absorption characteristic or an index characteristic of the material inside of the test subject or the aging of the distribution.

An optical system for measuring metabolism in a body according to the present invention includes a light source for generating rays of light having respective wavelengths to be irradiated to a test subject, an apparatus for irradiating the rays of light having respective wavelengths to a single or plural spots of the test subject, an apparatus for detecting the light passed through the test subject at a single or plural spots of the test subject, an apparatus for separating the detected light by wavelength, and optical transmitting means composed of an optical fiber. The apparatus for detecting the light is composed of a single or plural light detectors for detecting intensity of the passed light or the aging of the intensity. The apparatus for separating the detected light by wavelength is composed of a single or plural spectroscopes for separating the rays of light having respective wavelengths substantially at one time. Further, the number of the wavelengths of the rays of light irradiated from the light source is equal to the number of the specific spots of the test subject. By switching the light switch located between the light source and the test subject, the rays of light having respective wavelengths are irradiated to all the specific spots of the test subject. Each time the light switch is switched, the light passed through the test subject is detected. The number of the specific spots of the test subject is smaller than the number of wavelengths of the rays of light irradiated from the light source. The specific spots of the test subject are divided into the same number of irradiation groups as the number of wavelengths of the rays of light to be irradiated to the specific spots of the test subject. By switching the optical switch located between the light source and the test subject, the rays of light having respective wavelengths are irradiated to each specific spot of the test subject in plural irradiation groups so as to detect the light passed through the test subject.

Moreover, an optical system for measuring metabolism in a body according to the present invention arranged to irradiate rays of light to the test subject for obtaining the information about the inside of the test subject includes a light source for generating rays of light having respective wavelengths, an apparatus for irradiating the mixture of the rays of light having respective wavelengths onto plural specific spots of the test subject, an apparatus for detecting the light passed through the test subject at plural detecting spots of the test subject, and an apparatus for separating the detected light by wavelength. The apparatus for irradiating light provides an apparatus for separating the light from the light source into plural wavelengths. Or, the pulse light may be the light irradiated to the test subject.

According to the present invention, the rays of light are irradiated from a large number of spots at one time. The wavelengths of the light passed through the test subject are dispersed by the spectroscope and are detected at a large number of spots of the test subject at one time. Hence, the measuring time can be reduced. If the light source generates the pulse light but does not irradiate the rays of light having respective wavelengths to the test subject one time, the times at which the rays of light are irradiated to the test subject as the pulse is generated are shifted according to each wavelength. This makes it possible to reduce the measuring time. In particular, to detect a minute light, as the number of the specific spots of the test subject, the number of the wavelengths of the irradiated rays of light, and the number of the detecting points of the light passed through the test subject are increased, the measuring time is made longer accordingly. In such a case, the present invention makes it possible to reduce the measuring time. For the conventional one measurement, by irradiating a ray having one wavelength to one specific spot of the test subject, the passed light is detected at one detection point. For one measurement of the present invention, the rays of light having respective wavelengths are irradiated to plural specific spots where light is irradiated at one time. Since the transmitted light is detected at plural spots at one time, the measuring time is remarkably reduced as compared with the conventional measurement.

In the case of applying this optical system for measuring metabolism in a body to a medical use, by reducing the measuring time, the burden placed on the test subject may be remarkably reduced. Further, the metabolism in a body makes it possible to follow the aging of the material amount, which may be used for accurate and quick diagnosis.

DESCRIPTION OF THE PREFERRED EMBODIMENTS

Embodiment 1

Figure 1:
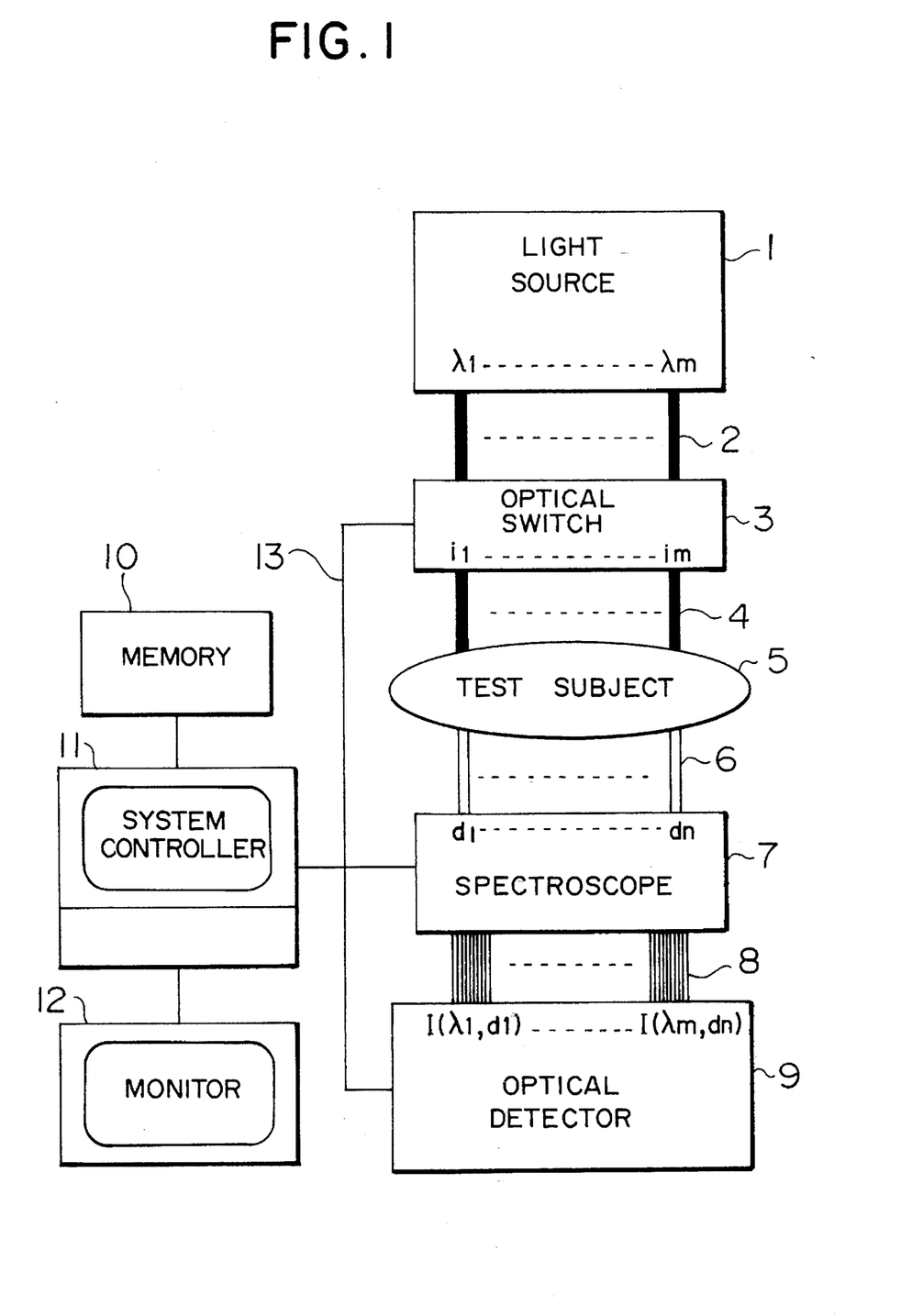
FIG. 1 is a block diagram showing a system arrangement according to a first embodiment of the present invention.

FIG. 1 shows an optical system for measuring metabolism in a body according to an embodiment of the present invention. A numeral 1 denotes a light source for generating m pulse rays of light (simply referred to as lights) or continuous wave light having respective wavelengths of $\lambda 1$ to $\lambda m$. m optical fibers 2 for transmitting light from the light source are connected to an optical switch 3 from which m optical fibers 4 for irradiating light are lead out. The optical fibers 4 for irradiating light are located around a tomographic surface of a test subject to be measured as an image. The light switch 3 serves to switch the connecting states between the optical fibers 2 for transmitting light from the light source and the optical fibers 4 for irradiating light. Around the cross section of the test subject 5 are located n optical fibers 6 for irradiating light, the ends of which are connected to a spectroscope 7. The spectroscope 7 provides m×n optical fibers 8 for a detection signal, the ends of which are connected to a photoelectronic device 9. The optical switch 3, the spectroscope 7 and the photoelectronic device 9 are controlled by a system controller 11. The measured data is recorded in a memory 10 through the system controller 11. Further, the measured result or the image obtained from the measured result is displayed on a monitor 12. The light source 1 operates to generate m lights, having respective wavelengths of $\lambda 1$ to $\lambda m$ at one time. The light of each wavelength is incident to each of the optical fibers 2 for transmitting light from the light source 2. If the light source 1 generates continuous spectrum light, like the embodiment 3 (see FIG. 7) to be described later, the continuous spectrum light is separated by the spectroscope according to wavelength. The light incident to the optical fiber 2 is led to enter into the optical fiber 4 connected to the optical fiber 2 through the optical switch 3. As a result, the m lights having respective wavelengths are irradiated to the test subject 5 through the optical fibers 4. The lights passed through the test subject are guided to the spectroscope 7 through the n optical fibers 6 for detecting lights. At one time, the mixed detected m lights passed through the test subject, each having the corresponding wavelength of $\lambda 1$ to $\lambda m$, travel through each fiber for detecting light. Since the specific spot of the test subject where light is irradiated corresponds to the corresponding wavelength, the lights that have travelled through the optical fibers 6 for detecting lights are dispersed by the spectroscope 7 so as to specify the specific spot of the test subject. As a spectroscope, a diffraction grating, a prism, a dichroic mirror and an interference filter may be used. The light which has been separated by wavelength is measured as m×n intensity signals of $I(\lambda 1, d1)$ to $I(\lambda m, dm)$ by the photoelectronic device 9. In FIG. 1, the expression of $I(\lambda i, dj)$ means that the light from the j-th optical fiber dj for detecting light is separated by wavelength and the light of the wavelength $\lambda i$ of the separated light is detected as light intensity $I(\lambda i, dj)$ by the photoelectric device. Like FIG. 1, the similar expression is used in FIGS. 3, 5, 7, 9 and 10 to be described later. These intensity signals are measured as time series data if necessary. The system controller 11 operates to process the measured data as an image by using an algorithm of an X-ray CT or an inverse problem solution.

Figure 2:
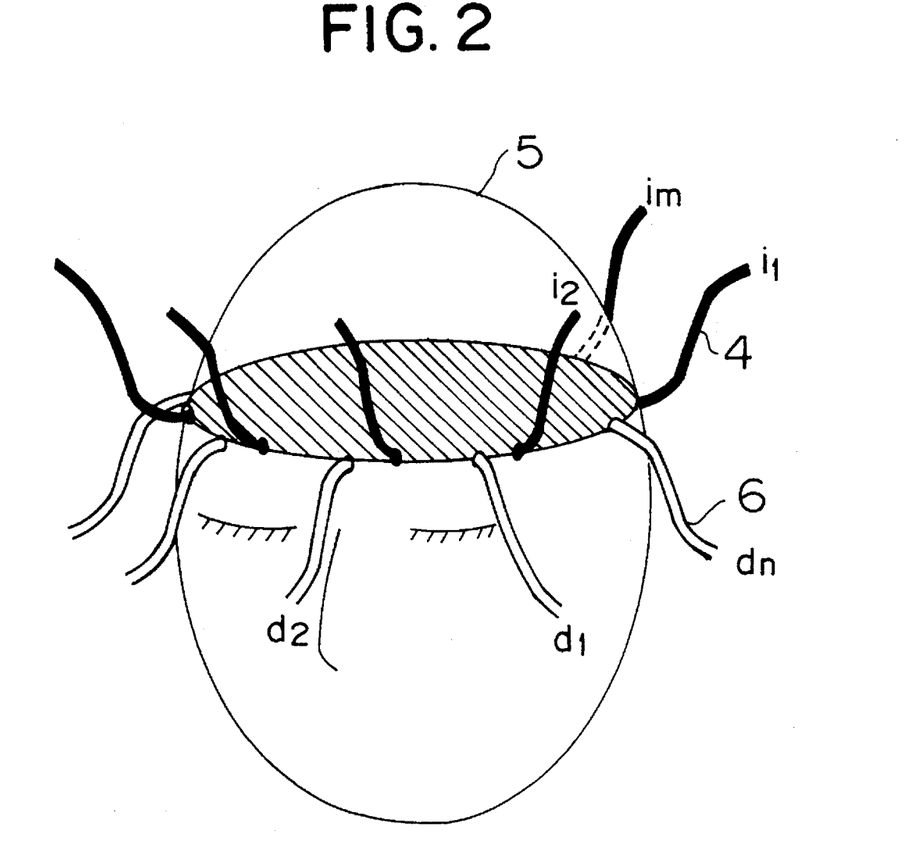
FIG. 2 is a view showing how an optical fiber for irradiating light and an optical fiber for detecting light are disposed in the first embodiment of the present invention.

FIG. 2 shows how m optical fibers 4 for irradiating light and n optical fibers 6 for detecting light located in the test subject 5. Since this embodiment needs to form a tomographic surface, the optical fibers 4 for irradiating light and the optical fibers 6 for detecting light are located on the tomogram to be obtained. Based on the intensity signal of the light passed through the test subject, the system controller 11 shown in FIG. 1 processes the data through the effect of the algorithm or an inverse problem solution of an X-ray CT so as to display a material amount or a value (amount) to be transformed from the material amount distributed inside of the test subject in the monitor 12 as a two-dimensional tomogram. In the embodiment 1 or the following embodiments, if the image to be formed is three-dimensional, it is necessary to locate the optical fibers 4 and 6 for irradiating light and detecting light so as to cover an image area to be required for a three-dimensional image. The intensity signal of the light passed through the test subject is processed at each of the two-dimensional tomographic layers. By piling plural two-dimensional tomographic layers, a three-dimensional image can be obtained. Further, the time change of an intensity signal of the light passed through the test subject is detected so that the material amount distributed inside of the test subject on the time or the value (amount) transformed from the material amount may be obtained as a two-dimensional tomogram so as to know the aging of the material amount or the value (amount) transformed from the material amount.

Figure 3:
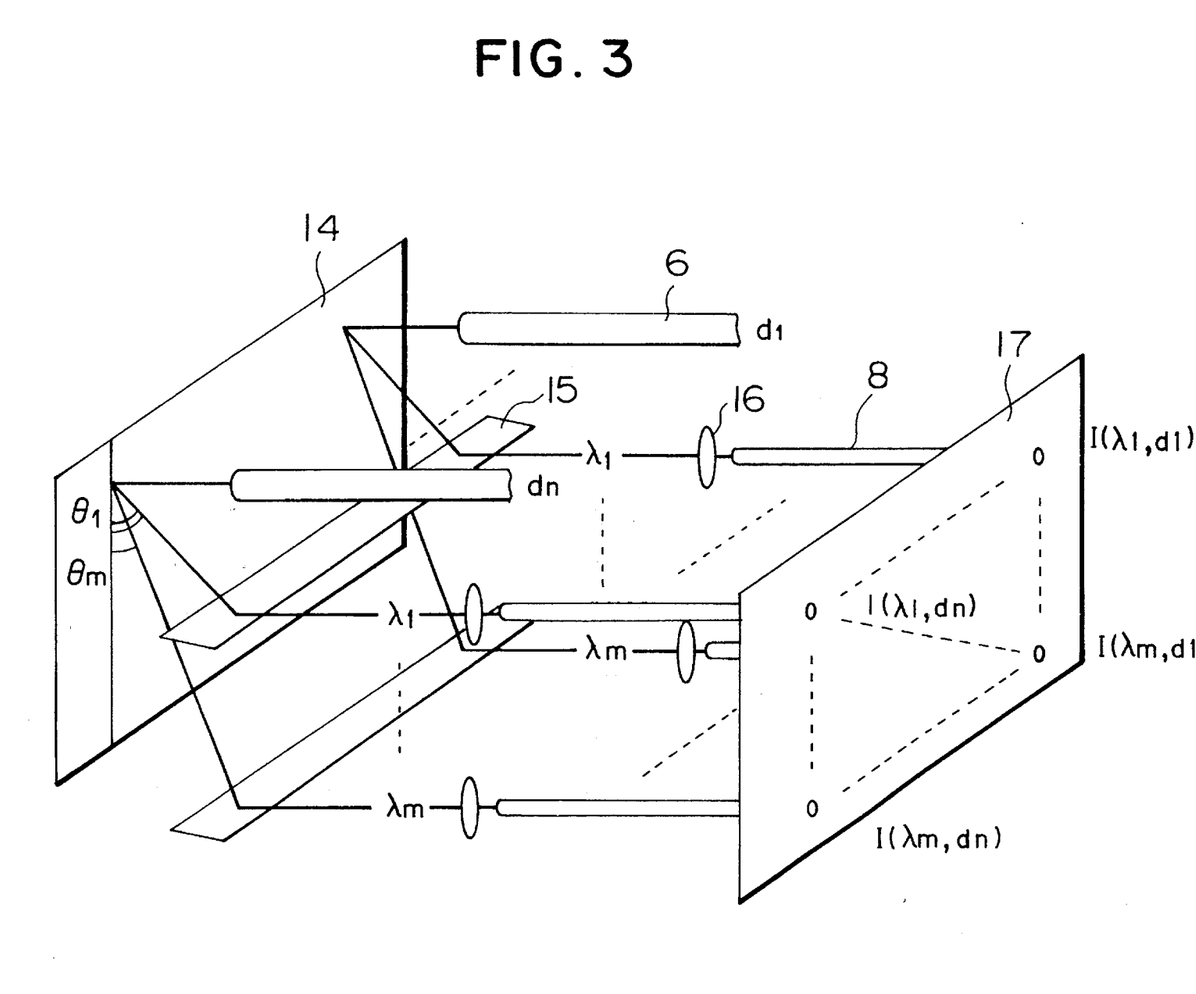
FIG. 3 is an explanatory view showing a method of dispersion using a diffraction grating according to the first embodiment of the present invention.

FIG. 3 shows a method of separation to be executed inside of the spectroscope 7 in the case of using the diffraction grating. The light passed through the test subject, incident to the optical fibers 6 for detecting light dk (k=1, . . . , n), is the mixture of the m lights, each having the corresponding wavelength of $\lambda 1$ to $\lambda m$. The mixed light incident to the diffraction grating 14 is separated into the light of each wavelength, because the reflective angles $\theta 1$ to $\theta m$ are related to the wavelengths $\lambda 1$ to $\lambda m$. The separated light is reflected on the reflective mirror 15 and condensed by a convergent lens 16 and reaches a light detection area 17 of the photoelectronic device.

Figure 4:
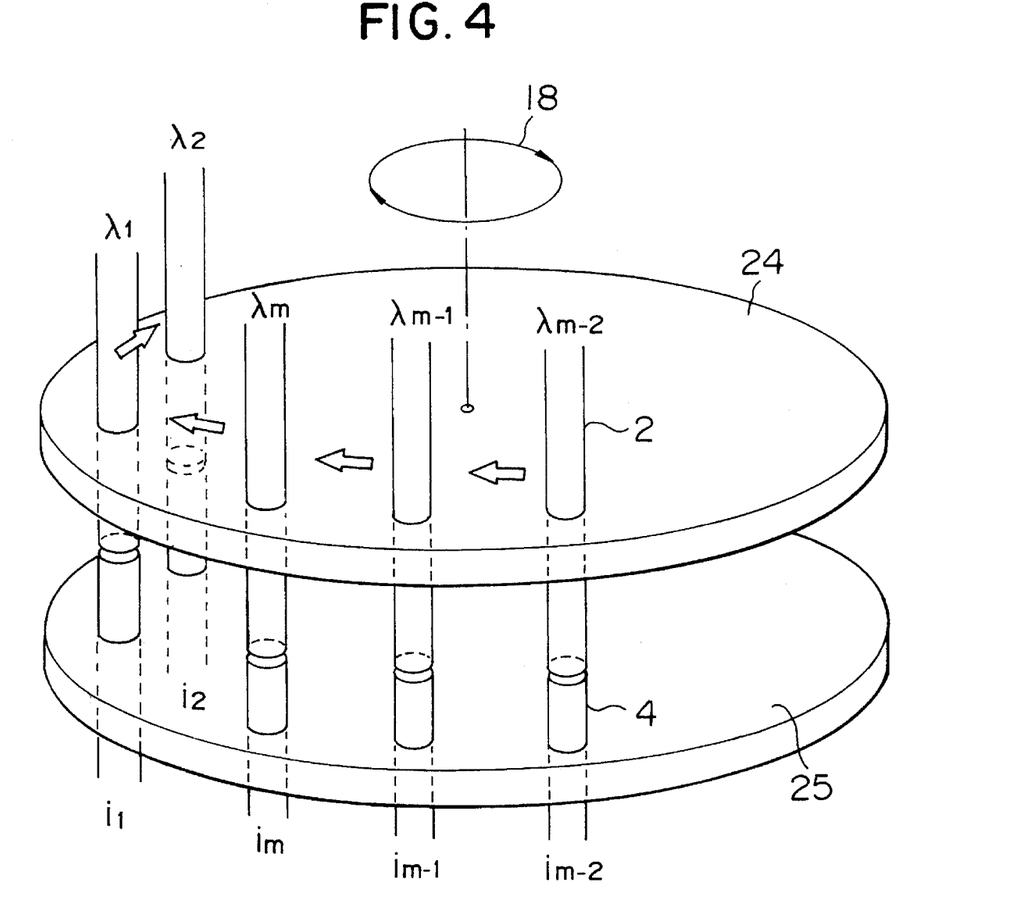
FIG. 4 is a view showing operation of a light switch in the first embodiment of the present invention.

FIG. 4 shows how the optical switch 3 operates. To quantify the material amount, this optical system for measuring metabolism in a body needs to use plural kinds of lights, each having the corresponding wavelength for one specific spot of the test subject. In this case, each time the light passed through the test subject is measured for each spot of the test subject, the light to be irradiated has another wavelength. As shown in FIG. 4, the optical switch 3 operates to switch the corresponding state between the optical fibers 2 for transmitting light from the light source and the optical fibers 4 for irradiating light. For example, after the first measurement, the optical switch 3 is rotated as viewed in FIG. 4 so that a holder 24 of the optical fibers 2 for transmitting light from the light source may be rotated against a holder 25 of the optical fibers 4 for irradiating light in the direction shown by arrow 18. As a result of this rotation, the connecting locations between the optical fibers 2 and the optical fibers 4 are switched so that the incident location of the light of the wavelength $\lambda 1$ may be switched from the optical fibers i1 to i2 and the incident location of the light of the wavelength $\lambda m$ is switched from the optical fibers im to i1, thus switching from a first irradiation pattern to a second irradiation pattern. With this switching, the m lights, each having the corresponding wavelength of $\lambda 1$ to $\lambda m$, are allowed to be irradiated to the corresponding specific spots of the test subject. For example, in a case in which three wavelengths are required for quantifying any material amount, it is just necessary to switch the optical switch 3 twice and to measure the amount three times, in which the number of measurements of the light passed through the test subject by switching the optical switch 3 is smaller than the number m of kinds of the wavelengths of the used lights. In a case that j wavelengths are required for quantifying any material amount, it is just necessary to switch the optical switch j-1 times, so as to irradiate j patterns, and measure the material amount j times, in which the relation of $j \leq m$ has to be established. Any optical switch may be used only if it may switch the corresponding relation between the optical fibers 2 for transmitting light from the light source and the optical fibers 4 for irradiating light so as to switch the irradiation pattern. The optical switch shown in FIG. 4 is an example. In this embodiment and the following embodiments, the corresponding relation between the optical fibers 2 and the optical fibers 4 is switched by the optical switch 3 based on control data for the optical switch pre-specified in the system controller 11. As described above, the optical switch 3, the spectroscope 7 and the optical detector 9 are controlled by the system controller 11. Each specific spot of the test subject corresponds to the corresponding wavelength of the light irradiated to this spot. The control data for the optical switch is stored in the memory 10 through the system controller 11. Hence, the lights guided out of the optical fibers for detecting light are dispersed so as to specify the specific spot of the test subject according to each wavelength of the lights.

Embodiment 2

Figure 5:
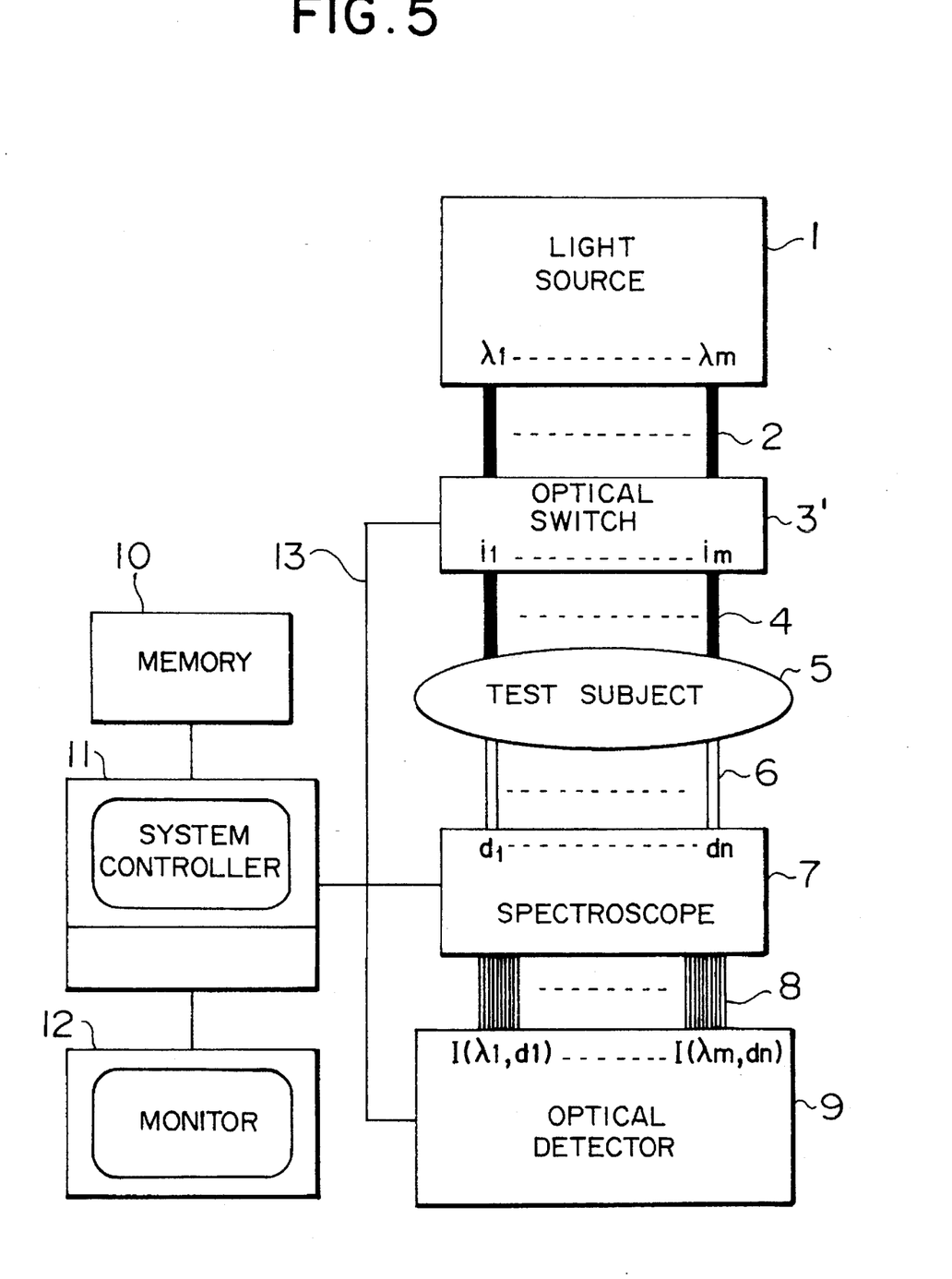
FIG. 5 is a block diagram showing a system arrangement according to a second embodiment of the present invention.

FIG. 5 shows an optical system for measuring metabolism in a body according to a second embodiment of the present invention. In this embodiment, the number of wavelengths generated by the light source is smaller than the number of the fibers for irradiating light located in the test subject. A numeral 1 denotes a light source for generating m pulse lights or continuous wave light, each having wavelengths of λ1 to λm. If the light source 1 uses a light source having continuous spectrum, like an embodiment 3 (see FIG. 7) to be described later, the continuous spectrum light is dispersed by the spectroscope for obtaining a continuous wave light. m optical fibers 2 for transmitting light from the light source 1 are connected to the optical switch 3'. The optical switch 3' provides k optical fibers 4 for irradiating light, which are located around the necessary tomographic surface of the test subject 5. The optical switch 3' is provided for switching the connecting state between the optical fibers 2 and the optical fibers 4. The other arrangement is the same as that shown in FIG. 1.

Figure 6:
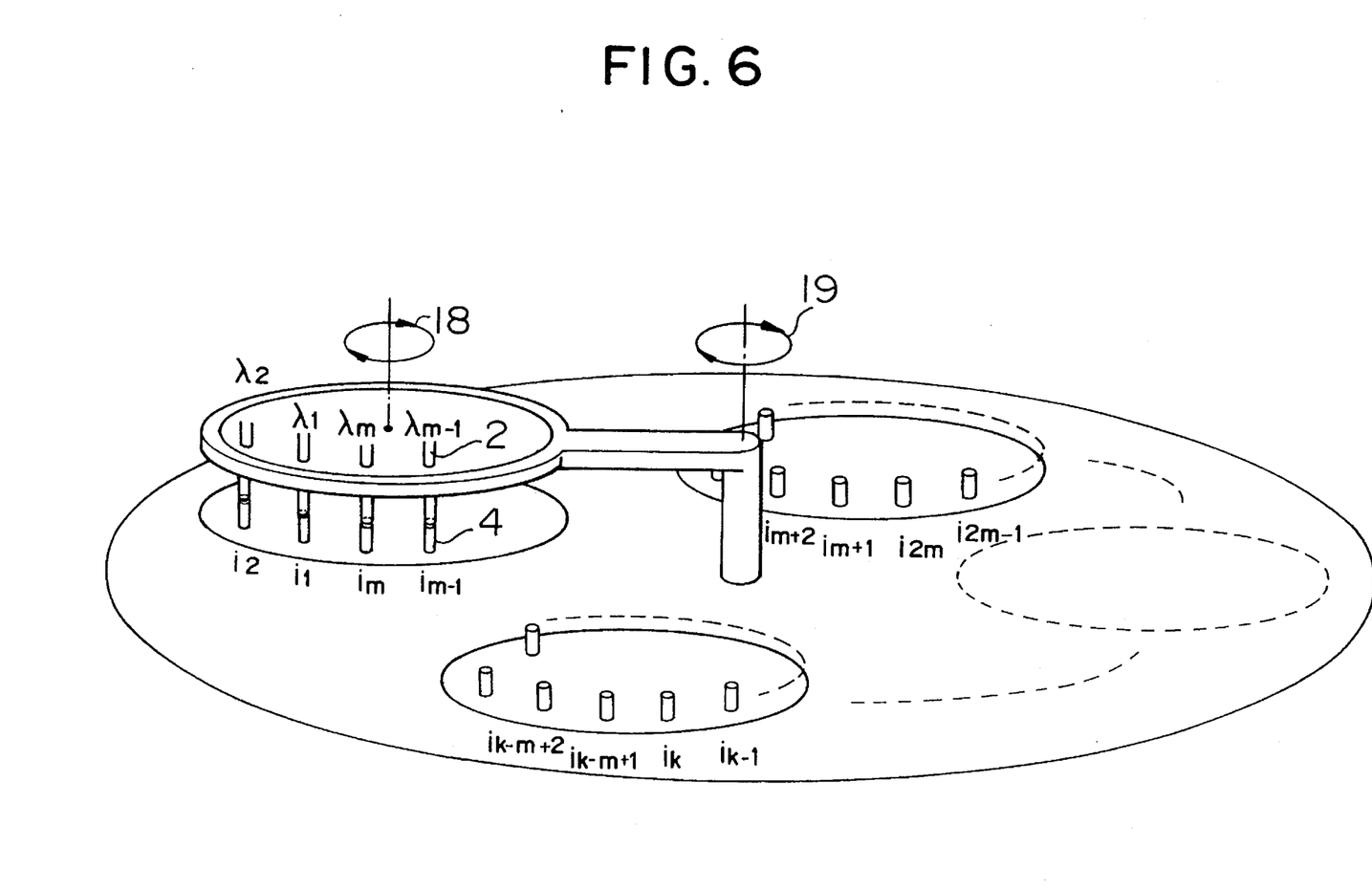
FIG. 6 is a view showing operation of a light switch included in the second embodiment of the present invention.

FIG. 6 shows how the optical switch 3' shown in FIG. 5 operates. In this embodiment, the optical switch 3' is arranged on the concept of a two-stage rotary switch. The optical switch 3' permits two kinds of rotation, as indicated by arrows 18 and 19, the rotation 18 for switching the connecting location between the optical fibers 2 for transmitting light from the light source and the optical fiber 4 for irradiating light and the rotation 19 for classifying the optical fibers for irradiating light as groups and selecting one or some groups. k optical fibers for irradiating light are classified as groups, each consisting of m fibers. If k is not evenly divisible by m, the last group contains less than m fibers. In the case of the first measurement of the light passed through the test subject to be done by switching the optical switch, with the rotation 18 of the optical switch, the light of the wavelength λ1 is applied to the optical fiber i1 for irradiating light, the light of the wavelength λ2 is applied to the optical fiber i2, . . . , the light of the wavelength λm is applied to the optical fiber im for measuring each wavelength. In the case of the second measurement of the light passed through the test subject to be done by the switching the optical switch, with the rotation 19, the optical switch is rotated so as to change the connecting state between the optical fibers 2 for transmitting light from the light source and the optical fibers 4 for irradiating light so that a group may be selected in sequence. As a result, the light of the wavelength λ1 is applied to the optical fiber λm+1 for irradiating light, . . . , the light of the wavelength λm is applied to the optical fiber i2m. As described above, the measurements of the light passed through the test subject to be done by switching the optical switch are repeated. On the termination of the final measurement, it means that the scan around the necessary tomographic surface is terminated. In a case of requiring the lights, each having the corresponding wavelength, to be irradiated to one specific spot of the test subject for quantifying the material amount inside of the test subject, with the rotation 18, the optical switch is operated so as to control the light having another wavelength to be incident to the specific spot of the test subject at the previous scan as described with respect to FIG. 4. The scan is done around the necessary tomographic surface as mentioned above.

Embodiment 3

Figure 7:
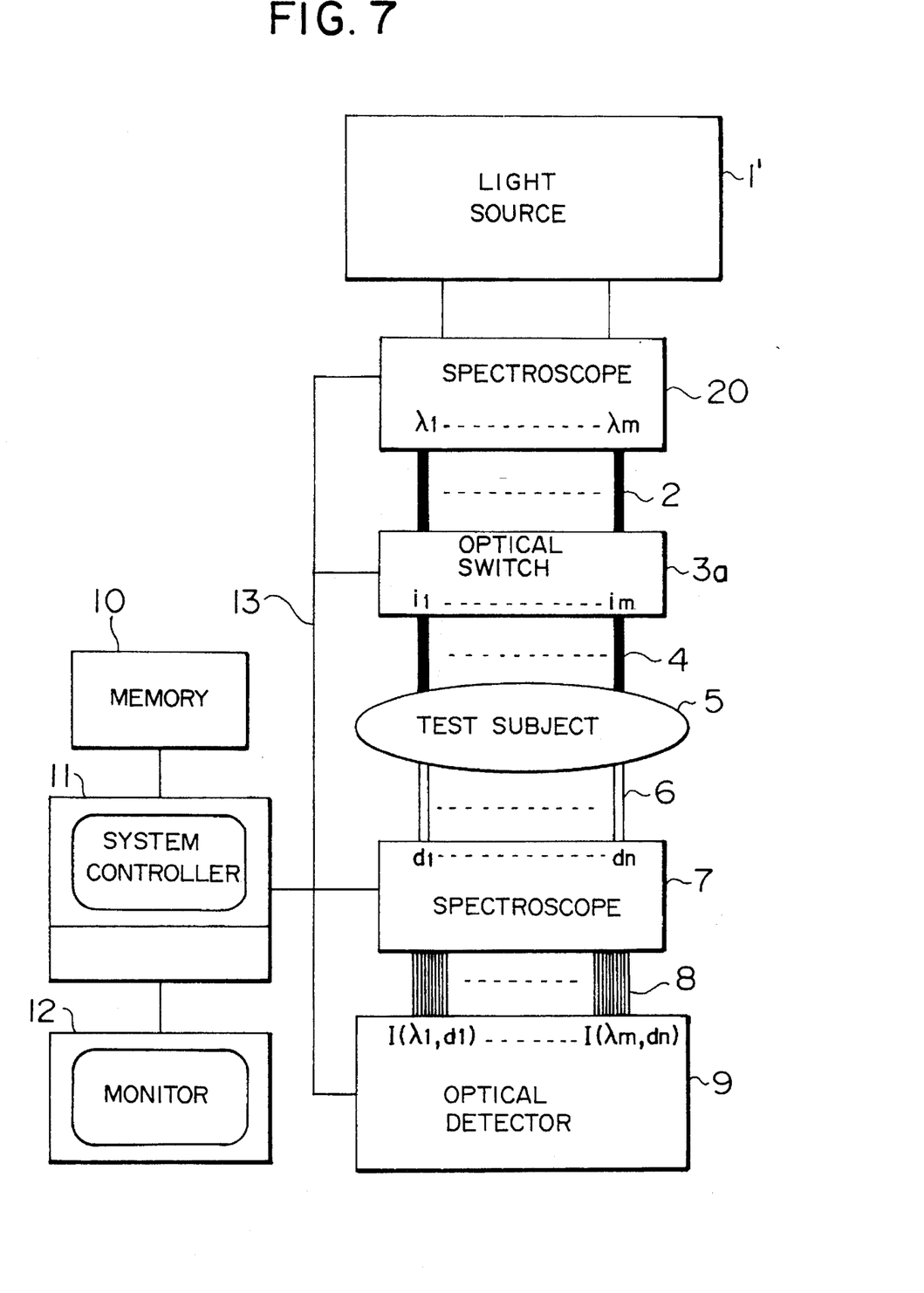
FIG. 7 is a block diagram showing a system arrangement according to a third embodiment of the present invention.

FIG. 7 shows an optical system for measuring metabolism in a body according to a third embodiment of the present invention. The light source 1' is a light source having continuous spectrum and for generating plural kinds of lights, each having the corresponding wavelength. The light generated in the light source 1' is entered into the spectroscope 20 in which the light is dispersed into the lights of m kinds of wavelengths of λ1, . . . , λm. The spectroscope 20 is connected to the optical switch 3a through m optical fibers 2 for transmitting light from the light source so that the lights having respective wavelengths may be entered into the optical fibers 2 one by one. The light incident to each optical fiber 2 is entered into each optical fiber 4 connected with the corresponding fiber 2 through the optical switch 3a. The optical switch 3a operates to switch the connecting state between the optical fibers 2 and the optical fibers 4 and may be the optical switch 3 or 3' described with respect to FIG. 4 or FIG. 6. The other arrangement shown in FIG. 7 is the same as that shown in FIG. 1.

Embodiment 4

Figure 8:
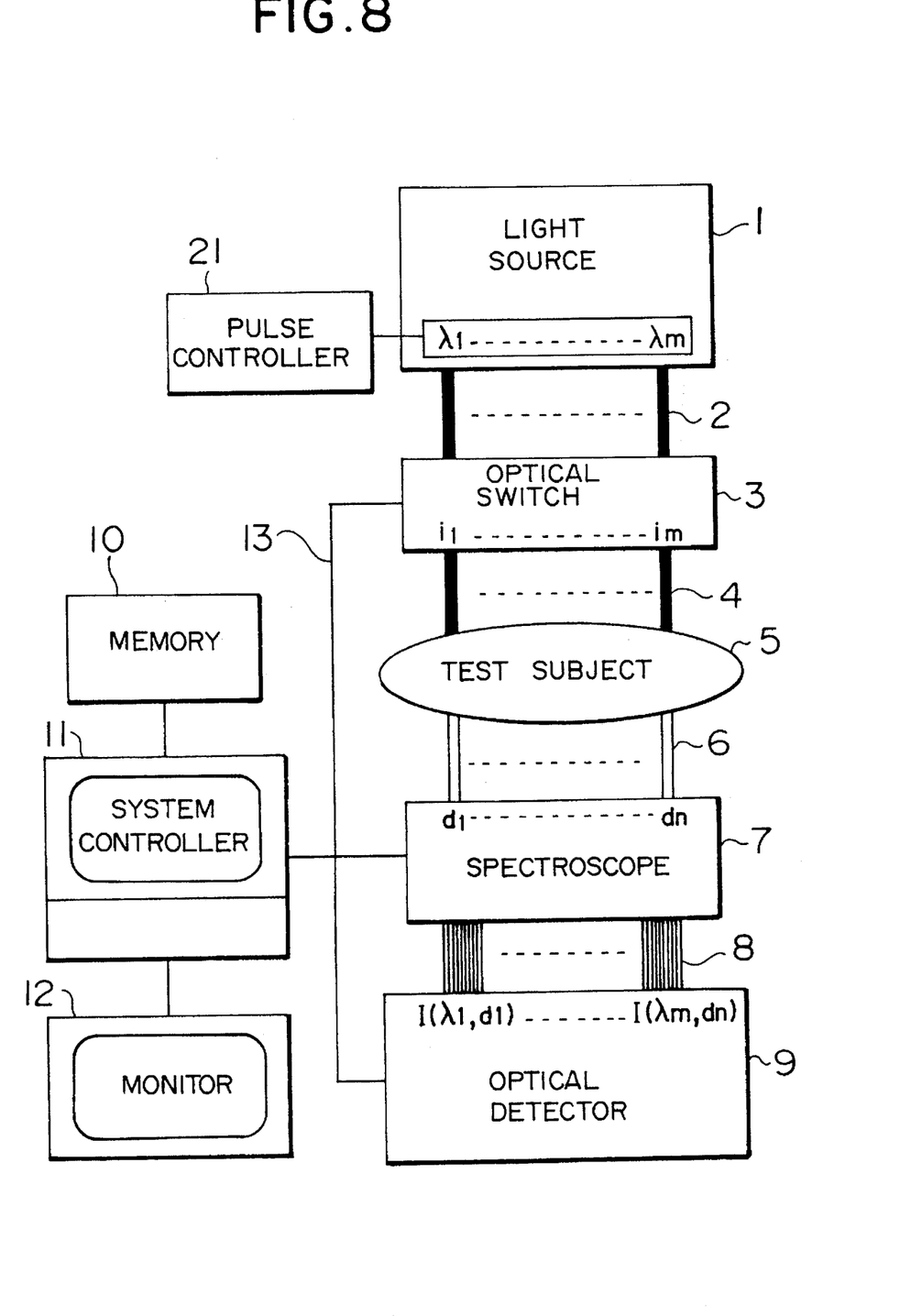
FIG. 8 is a block diagram showing a system arrangement according to a fourth embodiment of the present invention.
Figure 9:
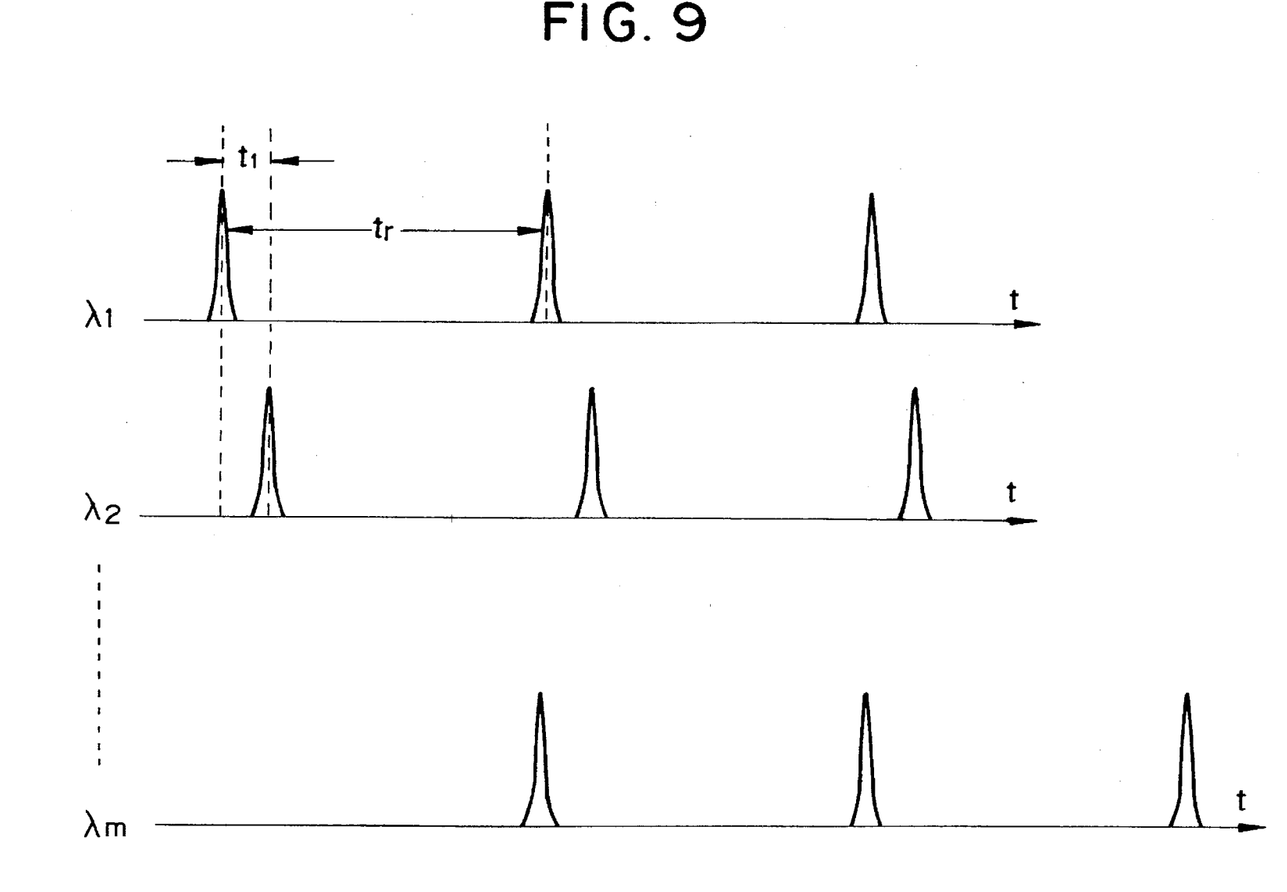
FIG. 9 is chart showing a timing of a light pulse generated in a light source in the fourth embodiment of the present invention.

FIG. 8 shows an optical system for measuring metabolism in a body according to a fourth embodiment of the present invention. A numeral 1 denotes a light source for generating m pulse lights, each having the corresponding wavelength of λ1 to λm. The light source 1 is connected to the m optical fibers for transmitting light from the light source through the optical switch 3. A numeral 21 denotes a pulse controller which is a device for controlling an occurrence time of light pulses generated by the light source 1. The pulse controller 21 operates to generate repetitive pulse lights having respective wavelengths λ1 to λm in any sequence. Each pulse light having its own wavelength is entered into the corresponding optical fiber 2. The light incident into each optical fiber 2 is led into the corresponding optical fiber 4 through the optical switch 3. As a result, m pulse lights having respective wavelengths are irradiated to the test subject 5 through the optical fibers 2 and 4. The optical switch 3 operates to switch the connecting location between the optical fibers 2 and 4 and may be the optical switch 3 described with respect to FIG. 4 or the optical switch 3' described with respect to FIG. 6. The other arrangement shown in FIG. 8 is the same as that shown in FIG. 1. FIG. 9 shows the timing on which the light pulses are generated. The pulse controller 21 operates to offset the occurrence time of the optical pulse of each wavelength by t1 second so as to repetitively generate the light pulse of each wavelength at a time interval of $t_r$.

Embodiment 5

Figure 10:
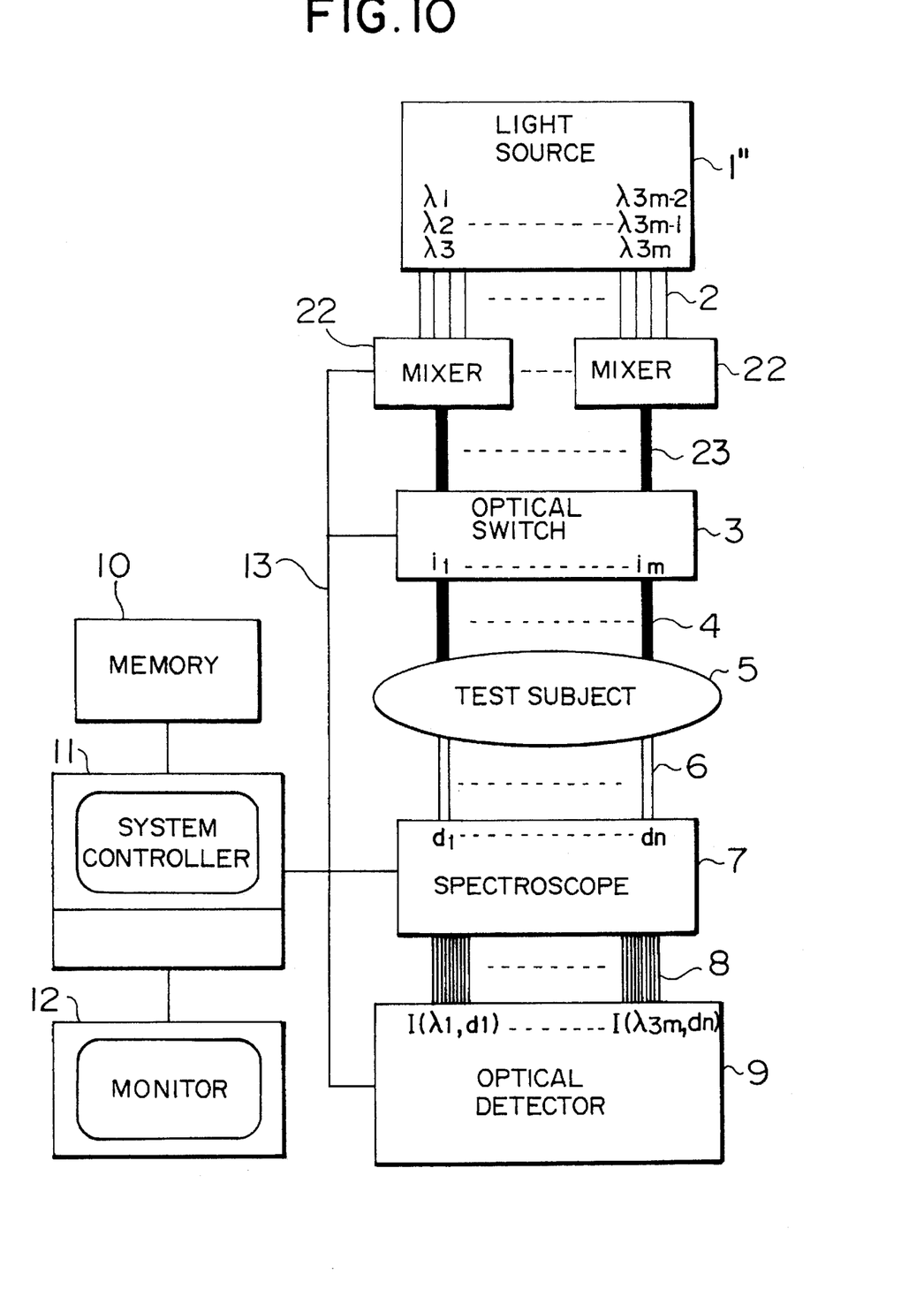
FIG. 10 is a block diagram showing a system arrangement according to a fifth embodiment of the present invention.

FIG. 10 shows an optical system for measuring metabolism in a body according to a fifth embodiment of the present invention. In this embodiment, the plural kinds of lights having respective wavelengths are irradiated from the same spot to the test subject at one time. The description will be oriented to the case requiring lights having three wavelengths for quantifying any material in the test subject. If the necessary number of wavelengths changes, the optical system may be easily extended. A numeral 1' denotes a light source for generating pulse lights or continuous wave light having 3m kinds of wavelengths λ1 to λ3m. If the light source 1' uses a light source having continuous spectrum, the continuous spectrum light is dispersed by the spectroscope so as to obtain the continuous wave light like the embodiment 3 (see FIG. 7) described above. The m combinations of three optical fibers for transmitting light from the light source are connected with the optical mixers 22. One optical fiber 23 is led out of each of m optical mixers 22 and is connected to the optical switch 3. The optical switch 3 provides m optical fibers 4 for irradiating light, which fibers are located around the necessary cross section of the test subject 5. The optical switch 3 operates to switch the connecting state between the optical fibers 2 and 4 and may be the optical switch 3 described in FIG. 4 or the optical switch 3' described in FIG. 6. Around the necessary tomographic surface of the test subject 5 are located n optical fibers 6 for detecting light. The ends of the optical fibers 6 are connected to the spectroscope 7. 3m×n optical fibers 8 for detecting light are led out of the spectroscope 7. The ends of the optical fibers 8 are connected to the optical detector 9. The optical switch 3, the spectroscope 7 and the optical detector 9 are controlled by the system controller 11. The measured data is stored in the memory 10 through the system controller 11. The measured result or the image obtained from the measured result is displayed on the monitor 12. The light source 1' generates 3m lights, each having the corresponding wavelength of λ1 to λ3m at one time. Each light of its own wavelength is entered into the corresponding optical fiber 2. One combination of three optical fibers 3 is connected to one optical mixer 22. The optical mixer 22 operates to mix the three kinds of lights with their own wavelengths and to send the mixed light to an optical fiber (optical transmitting system) 23. The light incident to the optical fiber 23 is led to the corresponding optical fiber 4 by means of the optical switch 3. As a result, the lights of three kinds of wavelengths are irradiated to the test subject through the optical fibers 4. The lights passed through the test subject are guided to the spectroscope 7 through n optical fibers 6 for detecting light. At this time, each optical fiber 6 for detecting light contains the mixture of the lights having the respective wavelengths λ1 to λ3m. Since each specific spot of the test subject where light is irradiated corresponds to a wavelength, the correspondence between the specific spot of the test subject and the detecting spot is able to be specified by dispersing the light travelled through the optical fibers 6 for detecting light with the spectroscope 7. The spectroscope 7 may be a diffraction grating, a prism, a dichroic mirror or an interference filter. The separated light may be measured as 3m×n intensity signals in the range of I(λ1, d1) to I(λ3m, dn) by means of the optical detector 9. These intensity signals are measured as data ranged on time series. Like the aforementioned embodiments 1 to 4, the system controller 11 processes the data as an image through the effect of the algorithm in the X-ray CT and the inverse problem solution provided. The optical system according to this embodiment is arranged to irradiate the necessary number of lights having their own wavelengths from one irradiating spot so that just one scan may be required for the test subject.

It goes without saying that the aforementioned embodiments may be modified in various forms. For example, each embodiment has been described with reference to arrangement in which plural rays of light are irradiated to plural specific spots of the test subject. It may be arranged so that a ray of light is irradiated to a single specific spot of the test subject for obtaining the internal information of the test subject.

In the optical switch as shown in FIGS. 4 and 6, to prevent loss of light transmission between each optical fiber for irradiating light and each optical fiber for transmitting light from the light source, the optical switch is located in a liquid crystal (for example, silicon oil) having a predetermined refractory index.

What is claimed is:

1. An optical system for measuring metabolism in a test subject by irradiating rays of light from a light source to the inside of the test subject and detecting rays of light passing from inside of the test subject so as to obtain information about the inside of the test subject, said optical system comprising:

irradiating means for receiving from the light source light having a plurality of wavelengths and irradiating plural rays of the light onto plural irradiation spots on the test subject, with each of the irradiation spots receiving a light ray of a different wavelength;

means for detecting rays of light passing from the inside of the test subject at plural detecting spots on the test subject; and first separating means for separating the detected rays of light by wavelength.

2. An optical system as claimed in claim 1, wherein said irradiating means irradiates rays of light having a wavelength in a range of from a visible wavelength to a near infrared wavelength.

3. An optical system as claimed in claim 1, wherein said irradiating means irradiates the plural rays of light onto the test subject substantially at one time.

4. An optical system as claimed in claim 1, wherein said irradiating means irradiates a plurality of pulses of light of different wavelengths, with the irradiating time of the pulses of the different wavelengths being varied according to the wavelength.

5. An optical system as claimed in claim 1, wherein said irradiating means includes second separating means for separating the received light by wavelength.

6. An optical system as claimed in claim 5, wherein said second separating means separates the received light into equally spaced wavelengths.

7. An optical system as claimed in claim 1, wherein each of the irradiation spots of the test subject onto which light is irradiated is specified by the wavelength of such irradiating light.

8. An optical system as claimed in claim 1, wherein said irradiating means comprises a first set of optical fibers positioned around the test subject for irradiating light onto the irradiation spots on the test subject, and said detecting means comprises a second set of optical fibers positioned around the test subject for detecting light from the detecting spots on the test subject.

9. An optical system as claimed in claim 1, further comprising intensity detecting means for detecting the intensity of the light from said first separating means.

10. An optical systems as claimed in claim 9, further comprising display means for displaying the spatial distribution of the material inside of the test subject based on the detected intensity of the light.

11. An optical system as claimed in claim 9, further comprising display means for displaying one of (i) the concentration of material inside of the test subject and (ii) a value transformed from the concentration of the material, as one of (i) a two-dimension and (ii) a three-dimensional tomographic image based on the detected intensity.

12. An optical system for measuring metabolism in a test subject by irradiating rays of light from a light source to the inside of the test subject and detecting rays of light passing from inside of the test subject so as to obtain information about the inside of the test subject, said optical system comprising:

irradiating means for receiving from the light source light having a plurality of wavelengths and irradiating plural rays of the light onto plural irradiation spots on the test subject, with each of the irradiation spots receiving a light ray of a different wavelength;

means for detecting rays of light passed from the inside of the test subject at plural detecting spots on the test subject;

a spectroscope for separating the detected rays of light by wavelength; and an optical detector for detecting the intensity of light from said spectroscope.

13. An optical system as claimed in claim 12, wherein said irradiating means irradiates light having a wavelength in a range from a visible wavelength to a near infrared wavelength.

14. An optical system as claimed in claim 12, wherein said irradiating means irradiates the rays of light onto the test subject substantially at one time.

15. An optical system as claimed in claim 12, wherein said irradiation means comprises means for irradiating a plurality of pulses of light, and control means for controlling irradiating times of the pulses.

16. An optical system as claimed in claim 15, wherein said control means varies the irradiating times of the pulses of lights according to their wavelengths.

17. An optical system as claimed in claim 12, wherein each of the irradiation spots of the test subject onto which light is irradiated is specified by the wavelength of such irradiated light.

18. An optical system as claimed in claim 12, wherein said irradiating means comprises a first set of optical fibers positioned around the test subject for irradiating light onto the irradiation spots on the test subject, and said detecting means comprises a second set of optical fibers positioned around the test subject for detecting light from the detecting spots on the test subject.

19. An optical system as claimed in claim 12, further comprising display means for displaying the spatial distribution of the material inside of the test subject based on the detected intensity of the light.

20. An optical system as claimed in claim 12, further comprising display means for displaying the concentration of material inside of the test subject, or a value transformed from the concentration of the material, as a two-dimensional or a three-dimensional tomographic image based on the detected intensity.

21. An optical system as claimed in claim 12, further comprising optical switching means for switching the rays of lights to be irradiated to the irradiation spots on the test subject so as to provide rays of desired wavelengths to each of the irradiation spots.

22. An optical system as claimed in claim 12, wherein said detecting means comprises a plurality of optical detectors, and each of said optical detectors detects intensity of a ray of light substantially at one time.

23. An optical system for measuring metabolism in a test subject by irradiating rays of light from a light source to the inside of the test subject and detecting rays of light passing from the test subject so as to obtain information about the inside of the test subject, said optical system comprising:

an optical switch for receiving from the light source light having a plurality of wavelengths and irradiating a plurality of rays of the light onto a plurality of irradiation spots on the test subject substantially at one time and in a first irradiation pattern, with each of the irradiating spots receiving a light ray of a different wavelength;

control means for controlling said optical switch to switch the rays of light irradiated onto the irradiation spots on the test subject so as to switch from the first irradiation pattern to a second irradiation pattern so that each of the plurality of irradiation spots can be irradiated by light rays of any of the plurality of wavelengths;

means for detecting a plurality of rays of light passing from the test subject at a plurality of detecting spots on the test subject; and separating means for separating the detected plurality rays of light by wavelength, the number of wavelengths in the plurality of wavelengths equaling the number of irradiated rays of the light in the plurality of irradiated rays of the light, the number of irradiation spots in the plurality of irradiation spots, the number of detected rays of light in the plurality of detected rays of light, and the number of detecting spots in the plurality of detecting spots.

24. An optical system for measuring metabolism in a test subject by irradiating rays of light from a light source to the inside of the test subject and detecting the rays of light passing from the test subject so as to obtain information about the inside of the test subject, said optical system comprising:

an optical switch for receiving from the light source rays of light having a plurality of wavelengths, dividing the received light rays into a plurality of groups, each group including a plurality of light rays, and irradiating one group of the plurality of groups of light rays onto a plurality of irradiation spots on the test subject substantially at one time in a first irradiation pattern, with each of the irradiation spots receiving light of a different wavelength, the number of irradiation spots in the plurality of irradiation spots equaling the number of light rays in said one group of light rays, and the number of wavelengths in the plurality of wavelengths being greater than the number of groups in the plurality of groups and greater than the number of light rays in the plurality of light rays;

control means for controlling said optical switch to switch the group of light rays irradiated onto the plurality of irradiation spots from said one group to another group of the plurality of groups, so that all the received light rays can irradiate irradiation spots of the test subject;

means for detecting rays of light passing from the test subject at a plurality of detecting spots on the test subject, the number of detecting spots equaling the number of irradiation spots; and means for separating the detected rays of light by wavelength.

25. An optical system as claimed in claim 24, wherein said control means further controls said optical switch to switch the rays of light within said one of the groups irradiated onto the third plurality of irradiation spots on the test subject so as to switch the irradiated pattern from the first irradiation pattern to a second irradiation pattern so that each of the irradiation spots on the test subject can be irradiated by light rays of any of the wavelengths.

26. An optical system for measuring metabolism in a test subject by irradiating a plurality of rays of light from a light source to the inside of the test subject and detecting rays of light passing from the test subject so as to obtain information about the inside of the test subject, said optical system comprising:

an optical switch for receiving from the light source light having a plurality of wavelengths and irradiating a plurality of rays of the light onto each irradiation spot of a group of irradiation spots made up of a plurality of irradiation spots on the test subject substantially at one time, with each of the irradiation spots receiving a light ray of a different frequency, the number of irradiation spots in the plurality of radiation spots equaling the number of rays of light in the plurality of rays of light, and the number of wavelengths in the plurality of wavelengths being greater than the number of rays of light in the plurality of rays of light;

control means for controlling said optical switch to switch the plurality of rays of light from irradiating a first group of irradiation spots to irradiating a second group of irradiation spots so that all irradiation spots on the test subject may be irradiated;

means for detecting the light rays passed through the test subject at plural detecting spots of the test subject; and separating means for separating the detected light rays by wavelength.

27. An optical system for measuring metabolism in a test subject by irradiating pulsed rays of light from a light source to the inside of the test subject and detecting pulsed rays of light passing from the test subject so as to obtain information about the inside of the test subject, said optical system comprising:

an optical switch for receiving from the light source pulsed rays of light of a plurality of wavelengths and irradiating a plurality of the pulsed rays of the light onto a plurality of irradiation spots on the test subject in a first irradiation pattern, with the irradiating times of the pulses of the different wavelengths being shifted according to the wavelengths, and with each of the irradiation spots receiving a pulsed light ray of a different wavelength;

control means for controlling said optical switch to switch rays of light irradiated onto the irradiation spots on the test subject so as to switch from the first irradiation pattern to a second irradiation pattern so that each of the plurality of irradiation spots can be irradiated by light rays of any of the plurality of wavelengths;

means for detecting a plurality of pulsed rays of light passing from the test subject at a plurality of detecting spots on the test subject; and separating means for separating the detected plurality of rays of light by wavelength, the number of wavelengths in the plurality of wavelengths equaling the number of irradiated pulsed rays of the light in the plurality irradiated of pulsed rays of the light, the number of irradiation spots in the plurality of irradiation spots, the number of detected pulsed rays in the plurality of detected pulsed rays, and the number of detecting spots in the plurality of detecting spots.

28. An optical system for measuring metabolism in a test subject by irradiating rays of light from a light source to the inside of the test subject and detecting the rays of light passing from the test subject so as to obtain information about the inside of the test subject, said optical system comprising:

an optical switch for receiving from the light source rays of light having a plurality of wavelengths, dividing the received light rays into a plurality of groups, each group including a plurality of light rays, and irradiating one group of the plurality of groups of light rays onto a plurality of irradiation spots on the test subject, with the irradiating times of the different wavelengths being shifted according to the wavelength, the number of irradiation spots in the plurality of irradiation spots equaling the number of light rays in said one group of light rays, and the number of wavelengths in the plurality of wavelengths being greater than the number of groups in the plurality of groups and greater than the number of light rays in the plurality of light rays;

control means for controlling said optical switch to switch the group of light rays irradiated onto the plurality of irradiation spots from said one group to another group of the plurality of groups, so that all the received light rays can irradiate irradiation spots of the test subject;

means for detecting rays of light passing from the test subject at a plurality of detecting spots on the test subject, the number of detecting spots equaling the number of irradiation spots; and means for separating the detected rays of light by wavelength.

29. An optical system as claimed in claim 28, wherein said control means further controls said optical switch to switch the rays within said one of said groups irradiated onto the third plurality of irradiation spots on the test subject so as to switch the irradiated pattern from the first irradiation pattern to a second irradiation pattern so that each of the irradiation spots on the test subject can be irradiated by light rays of any of the wavelengths.

30. An optical system for measuring metabolism in a test subject by irradiating pulsed rays of light from a light source to the inside of the test subject and detecting pulsed rays of light passing from the test subject so as to obtain information about the inside of the test subject, said optical system comprising:

an optical switch for receiving from the light source pulsed rays of light of a plurality of wavelengths and irradiating a plurality of the received pulsed rays of the light onto each irradiation spot of a plurality of irradiation spots on the test subject in a first radiation pattern, with the irradiating times of the pulses of the different wavelengths being shifted according to the wavelengths, and with each of the plurality of irradiation spots receiving a light ray of a different frequency, the number of irradiation spots in the plurality of irradiation spots equaling the number of irradiated pulsed rays in the plurality of irradiated pulsed rays, and the number of wavelengths in the plurality of wavelengths being greater than the number of irradiated pulsed rays in the plurality of irradiated pulsed rays;

control means for controlling said optical switch to switch the plurality of irradiated pulsed rays from irradiating a first group of irradiation spots to irradiating a second group of irradiation spots so that all irradiation spots on the test subject may be irradiated;

means for detecting a plurality of pulsed rays of light, equal in number to the number of irradiated pulsed rays in the plurality of irradiated pulsed rays, the plurality of detected pulsed rays of light passing from the test subject at a plurality of detecting spots on the test subject equal in number to the number of irradiated pulsed rays in the plurality of irradiated pulsed rays; and separating means for separating the plurality of detected pulsed rays of light by wavelength.

31. An optical system for measuring metabolism in a test subject by irradiating rays of light from a light source to the inside of the test subject and detecting rays of light passing from the test subject so as to obtain information about the inside of the test subject, said optical system comprising:

an optical switch for receiving from the light source light having a plurality of wavelengths and irradiating rays of the light onto corresponding irradiation spots on the test subject in a first irradiation pattern, with each of the irradiating spots receiving a light ray of a different wavelength;

control means for controlling said optical switch to switch the rays of light irradiated onto the irradiation spots on the test subject so as to switch from the first irradiation pattern to a second irradiation pattern so that each of the first plurality of irradiation spots can be irradiated by light rays of any of the first plurality of wavelengths;

means for detecting rays of light passing from the test subject at plural detecting spots on the test subject; and separating means for separating the detected rays of light by wavelength.

32. An optical system for measuring metabolism in a test subject by irradiating rays of light from a light source to the inside of the test subject and detecting rays of light passing from the test subject so as to obtain information about the test subject, said optical system comprising:

irradiating means for receiving from the light source light having a plurality of wavelengths and irradiating rays of the light onto a plurality of irradiation spots on the test subject, with each of the irradiation spots receiving a light ray of a different wavelength;

means for detecting rays of the light passing from the test subject at plural detecting spots; and separating means for separating the detected light by wavelength.

33. An optical system as claimed in claim 32, wherein said irradiating means includes means for separating rays of received light by wavelength.

34. An optical system as claimed in claim 32, wherein said irradiation means includes means for pulsing the irradiated light to provide pulsed rays of light.

* * * * *